(12) United States Patent
Lewis et al.

(10) Patent No.: US 10,018,547 B2
(45) Date of Patent: Jul. 10, 2018

(54) IMAGING MICROVISCOMETER

(71) Applicant: MALVERN INSTRUMENTS INC., Westborough, MA (US)

(72) Inventors: E. Neil Lewis, Olney, MD (US); Kenneth Haber, Frederick, MD (US); John McCaffrey, Columbia, MD (US); Vishal Patil, Columbia, MD (US); Samiul Amin, Ellicott City, MD (US); Rohit Goswami, Columbia, MD (US)

(73) Assignee: Malvern Instruments Limited, Malvern (GB)

( * ) Notice: Subject to any disclaimer, the term of this patent is extended or adjusted under 35 U.S.C. 154(b) by 175 days.

(21) Appl. No.: 14/769,149

(22) PCT Filed: Feb. 20, 2014

(86) PCT No.: PCT/GB2014/050505
§ 371 (c)(1),
(2) Date: Aug. 20, 2015

(87) PCT Pub. No.: WO2014/128478
PCT Pub. Date: Aug. 28, 2014

(65) Prior Publication Data
US 2015/0377758 A1    Dec. 31, 2015

Related U.S. Application Data

(63) Continuation of application No. 13/773,259, filed on Feb. 21, 2013, now abandoned, and a continuation of
(Continued)

(51) Int. Cl.
*G01N 11/06* (2006.01)
*G01N 11/04* (2006.01)
*G01N 11/00* (2006.01)

(52) U.S. Cl.
CPC .............. *G01N 11/06* (2013.01); *G01N 11/04* (2013.01); *G01N 2011/008* (2013.01)

(58) Field of Classification Search
None
See application file for complete search history.

(56) References Cited

U.S. PATENT DOCUMENTS 4,370,413 A * 1/1983 Neeman ............... G01N 33/579
422/534
4,679,427 A * 7/1987 Kanda .................... G01N 11/16
73/54.26
(Continued)

FOREIGN PATENT DOCUMENTS

GB      2304408      9/1997
WO      9910724      4/1999
WO      2013005185   1/2013

OTHER PUBLICATIONS

PCT International Preliminary Report on Patentability/PCT Written Opinion, PCT/GB2014/050505, International filing date Feb. 20, 2014, Report dated Apr. 19, 2016.
(Continued)

*Primary Examiner* — Kate Luo
(74) *Attorney, Agent, or Firm* — Kristofer E. Elbing

(57) ABSTRACT

Viscometers and viscometry methods are disclosed. In one general aspect, a fluid is driven through capillary tubes with different inside volumes, and successive images of the fluid are acquired as it advances through the inside volume of the capillary tubes. A range of different viscosity values of the fluid are derived from the successive acquired images, and results of this step are reported in a manner that provides insight into non-Newtonian effects in the fluid. In another general aspect, a viscosity value is selected based on detected pressure levels.

42 Claims, 7 Drawing Sheets

Related U.S. Application Data application No. 13/842,378, filed on Mar. 15, 2013, now abandoned.

(60) Provisional application No. 61/937,460, filed on Feb. 7, 2014.

(56) References Cited

U.S. PATENT DOCUMENTS

| | | | |
|---|---|---|---|
| 4,688,099 A * | 8/1987 | Funston | H04N 5/253 348/104 |
| 5,959,195 A | 9/1999 | Gottfert | |
| 6,428,488 B1 | 8/2002 | Kensey et al. | |
| 2001/0044584 A1* | 11/2001 | Kensey | A61B 5/02028 600/504 |
| 2002/0007664 A1 | 1/2002 | Shin et al. | |
| 2002/0088953 A1 | 7/2002 | Kensey | |
| 2003/0182991 A1 | 10/2003 | Spaid et al. | |
| 2004/0252304 A1* | 12/2004 | Goix | G01N 15/147 356/417 |
| 2005/0087001 A1* | 4/2005 | Irani | G01N 11/08 73/54.04 |
| 2005/0132879 A1 | 6/2005 | Grollimund et al. | |
| 2005/0170521 A1 | 8/2005 | Archibald | |
| 2006/0065044 A1* | 3/2006 | Tsang | G01N 11/06 73/54.07 |
| 2007/0066794 A1* | 3/2007 | Jernigan | C08G 63/85 528/274 |
| 2008/0112029 A1 | 5/2008 | Bodkin | |
| 2008/0269668 A1* | 10/2008 | Keenan | A61K 49/223 604/24 |
| 2009/0282901 A1* | 11/2009 | Leonard | G01N 11/06 73/54.02 |
| 2012/0206602 A1 | 8/2012 | Clucas et al. | |
| 2012/0236302 A1* | 9/2012 | Rutowska | G01N 11/04 356/301 |
| 2013/0038727 A1* | 2/2013 | Clark | C12M 41/14 348/143 |

OTHER PUBLICATIONS

PCT International Search Report, PCT/GB2014/050505, International filed Feb. 20, 2014, ISR dated Apr. 18, 2016.

* cited by examiner

IMAGING MICROVISCOMETER

This application is related to application Ser. No. 13/773,259, filed Feb. 21, 2013, and application Ser. No. 13/842,378, filed Mar. 15, 2013, which are both herein incorporated by reference.

FIELD OF THE INVENTION

This invention relates to methods and apparatus for detecting properties of fluids, including viscosity, shear rate, and spectral characteristics.

BACKGROUND OF THE INVENTION

Lensless microfluidic detection techniques have been proposed to acquire microscopic images of samples such as biological materials and cells. They operate by acquiring images of suspended samples in close proximity to a high-resolution imaging detector. Their small size has resulted in their use being proposed in a variety of life science applications, including microscopes, smart petri dishes, and point-of-care diagnostic systems.

SUMMARY OF THE INVENTION

According to a first aspect of the invention, there is provided a viscometer comprising: a source of fluid pressure, a first tube having an inside volume that is hydraulically responsive to the source of fluid pressure, a first array of optical detectors positioned along a length of the first tube with a plurality of its detectors optically responsive to the inside volume of the first tube and including an image data output, an acquisition driver circuit responsive to the image data output of the first array to acquire a series of successive images of the inside volume of the first tube, and viscosity computation logic responsive to the acquisition driver circuit and operative to compute the viscosity of a fluid flowing along the first tube from the series of images of the inside volume of the first tube.

The viscometer may further comprise a second tube having an inside volume that is hydraulically responsive to the source of fluid pressure, and a second array of optical detectors positioned along a length of the second tube with a plurality of its detectors optically responsive to the inside volume of the second tube and including an image data output. The acquisition driver is responsive to the image data output of the second array to acquire a series of images of the inside volume of the second tube. The viscosity computation logic is operative to compute the viscosity of a fluid flowing along the second tube from the series of images of the inside volume of the second tube.

The use of a second tube may provide increased accuracy, by verifying the measurement from the first tube.

The source of fluid pressure may be configured to provide a common pressurized fluid to the inside volumes of the first and second tubes. The first and second arrays of detectors may be part of a two-dimensional array detector. Such a two-dimensional array may provide a low cost, high accuracy method of measuring the movement of the liquid within the tubes.

The first array of detectors may be a two-dimensional array of optical detectors. The first and second arrays of detectors may be one-dimensional arrays of optical detectors. The first one dimensional array of detectors may be part of a first one-dimensional array detector and the second one-dimensional array of detectors may be part of a second one-dimensional array detector.

The inside volume of the first tube may be larger than the inside volume of the second tube. The second tube may have a cross sectional area that is different to a cross sectional area of the first tube. The use of two tubes with different cross sectional area may provide insight into non-Newtonian effects. For instance, variations in apparent viscosity with tube diameter can be related to non-Newtonian fluid properties.

The viscometer may further include shear rate computation logic responsive to the acquisition driver circuit and operative to compute a shear rate of the fluid from the succession of images of the inside volumes of the first and second tubes.

Further tubes may be included, each having an inside volume responsive to the source of fluid pressure, wherein a cross sectional area of the first tube and the further tubes are all different from each other. The first array of optical detectors may also be positioned proximate the further tubes with further pluralities of the array detectors each being optically responsive to the inside volumes of one of the further tubes. Shear rate computation logic may be provided, responsive to the acquisition driver circuit and operative to compute a shear rate of the fluid from the succession of images of the inside volumes of the first tube and the further tubes.

As an alternative to having different cross sectional areas, an inside volume of the first tube and the further tubes may all be different from each other. The use of further tubes may allow non-Newtonian properties of the fluid to be inferred, for example based on variations in apparent fluid viscosity with varying tube cross sectional area.

The first and further tubes may be placed side-by-side where they are proximate the first array of optical detectors, and are bundled at the open end. A side by side arrangement of narrow tubes with a two dimensional detector provides for a cost effective viscometer that can measure non-Newtonian fluid properties. The viscosity computation logic may be operative to compute the viscosity based on detected movement of a meniscus in the first tube. The viscosity computation logic is operative to compute the viscosity based on a pixel size and frame rate.

The viscometer may further include calibration storage for calibration information about a calibration run with a calibration standard, and where the viscosity computation logic is responsive to the calibration information stored in the calibration storage. Storing such calibration information enables the viscometer to automatically compare any results obtained against a calibrated standard, thereby providing accurate (and potentially traceable) results.

The viscometer may further include at least one calibration tube having an inside volume that is hydraulically responsive to at least one source of a known fluid standard and wherein the two-dimensional array of optical detectors includes a plurality of detectors that are optically responsive to the inside volume of the calibration tube.

The viscometer of any preceding claim wherein the first tube has a diameter below 500 µm. The array of optical detectors may comprise at least one of: visible light detectors; infrared light detectors, and ultraviolet light detectors. The filter may be positioned in an optical path between the first tube and the first array of optical detectors. The filter may be a variable filter, and the viscometer may further include spectrum derivation logic responsive to the first array of optical detectors. The filter may be a bandpass filter.

An optical path between the first array of optical detectors and the first tube does not include a lens. A lenseless arrangement may result in a low cost system. A pressure transducer may be provided, responsive to the source of fluid pressure. The viscosity computation logic may be responsive to the pressure transducer and operative to compute a pressure-corrected viscosity. The viscometer may include viscosity value selection logic responsive to the pressure transducer and wherein the viscosity value selection logic is operative to select a viscosity value based on detected pressure levels. The viscosity value selection logic is operative to exclude outliers. The use of a pressure sensor allows pressure corrected viscosity to be determined, improving accuracy. Excluding outliers further improves the quality of the measurement. The viscosity value selection logic may be operative to seek stable periods.

The viscometer may further include a multiply strobed illumination source to illuminate at least one of the tubes. The use of a strobed illumination source provides for high intensity illumination, while making efficient use of power. The viscometer may include a multilevel strobed illumination source to illuminate at least one of the tubes.

According to a second aspect of the invention, there is provided a viscometer, comprising: a syringe body defining a pumped volume between a plunger opening and a needle outlet, a syringe needle defining an injection channel that is hydraulically connected to the needle outlet of the syringe body, a plunger positioned to reciprocate within the syringe body, an actuator operative to advance the plunger, a force measurement gauge mechanically coupled to the plunger, and viscosity computation logic responsive to the force measurement gauge and operative to compute the viscosity of a fluid sample in the syringe body. The force measurement gauge may be a load cell and/or the force measurement gauge may include a strain gauge.

According to a third aspect of the invention there is provided a viscometry method, comprising: driving a fluid under test through an inside volume of a first tube, pulsing an illumination source, acquiring successive images of the fluid under test as it advances through the inside volume of the first tube and is illuminated by the step of pulsing an illumination source, and deriving a viscosity of the fluid under test from the successive acquired images of the fluid under test as it advances through the inside volume of the first tube.

The step of pulsing may pulse the source once during an acquisition. Synchronizing each illumination pulse with each acquisition may increase efficiency of illumination. The step of pulsing may pulse the source a plurality of times during an acquisition. The step of pulsing may pulse the source with different levels of intensity during an acquisition.

According to a fourth aspect of the invention, there is provided a viscometry method, comprising: driving a fluid under test through an inside volume of a first tube, acquiring successive images of the fluid under test as it advances through the inside volume of the first tube, and deriving a viscosity of the fluid under test from the successive images of the fluid under test as it advances through the inside volume of the first tube.

The method may comprise acquiring a succession of pressure values for the fluid under test, wherein deriving the viscosity of the fluid under test is performed based on the successive images of the fluid under test and the succession of pressure values. The steps of acquiring pressure values and acquiring images take place substantially synchronously.

The method may include the step of driving the fluid under test through an inside volume of one or more further tubes, acquiring successive images of the fluid under test as it advances through the inside volume of the first tube and the inside volumes of the further tubes, and deriving a shear rate of the fluid from the image data of the fluid under test as it advances through the inside volume of the first tube and the further tubes. The method may include the step of recovering the fluid under test from the first tube after the step of acquiring. The method may further include the following calibration steps performed before the step of driving a fluid under test through the inside volume of the first tube: driving a fluid calibration standard through an inside volume of the first tube; acquiring successive image data of the fluid calibration standard under test as it advances through the inside volume of the first tube, and deriving calibration information from the successive acquired images of the fluid calibration standard as it advances through the inside volume of the first tube. The step of deriving a viscosity of the fluid under test may derive the viscosity of the fluid under test from calibration information and the image data acquired from the fluid under test as it advances through the inside volume of the first tube.

The method may be operative to derive a viscosity of a sample of less than 10 microliters. The method may further including the step of introducing a dye in the fluid under test. The fluid within the tube may thereby be more reliably and/or accurately tracked. The step of acquiring successive images of the fluid under test as it advances through the inside volume of the first tube may be sensitive to the dye.

The method may further include the step of deriving a spectrum of the fluid under test as it advances through the inside volume of the first tube.

According to a fifth aspect of the invention there is provided a viscometer, comprising: means for driving a fluid under test through an inside volume of a first tube, means for acquiring successive image data of the fluid under test as it advances through the inside volume of the first tube, and means for deriving a viscosity of the fluid under test from the successive acquired images of the fluid under test as it advances through the inside volume of the first tube.

The viscometer may further comprise means for acquiring a succession of pressure values for the fluid under test. The means for deriving a viscosity of the fluid may derive the viscosity of the fluid under test from the succession of pressure values and the successive acquired images of the fluid under test as it advances through the inside volume of the first tube.

According to a sixth aspect of the invention there is provided a viscometry method, comprising: driving a plunger to drive a fluid under test through an inside volume of a syringe needle, acquiring successive positions for the fluid under test as it is driven through the inside volume of the syringe needle, measuring forces on the fluid during the steps of driving and acquiring, and deriving at least one property of the fluid under test from the measured forces and the acquired successive positions for the fluid under test as it advances through the inside volume of the first tube.

The step of deriving may derive viscosity as the one property of the fluid under test.

According to a seventh aspect of the invention, there is provided a viscometry method, comprising: driving a fluid under test through an inside volume of a first tube, acquiring successive positions for the fluid under test as it advances through the inside volume of the first tube, and deriving rheological information for the fluid under test from differences in velocity detected in the step of acquiring successive positions.

The derived rheological information may include a yield stress for the fluid under test and/or an extensional viscosity. The step of driving may be performed by a plunger and the successive positions are positions of a portion of the plunger. The step of driving may be performed at different pressures. The step of acquiring positions may include a step of acquiring images of the fluid under test in the tube.

The viscometer may comprise rheological information derivation logic responsive to the acquisition driver circuit and operative to derive rheological information from the fluid from changes in velocity of the fluid under test detected in the succession of images of the inside volume of the first tube. The viscometer may be a capillary viscometer, and the first, second, further and/or calibration tubes may be a first capillary tube. Different types and sizes of tubes can be used. In some embodiments the tube may be a capillary tube, but this is not essential, and other tubes may be used. The material of the tube is preferably transparent to a wavelength of light that the optical detectors are responsive to. The contact angle of a fluid sample with the internal surface of the tube may not limit the type of tube that is suitable. The tube may comprise a glass and/or polymeric material. The lumen through the tube may be circular, or may be another shape. For example, a rectangular and/or square cross section may be appropriate. The diameter (or longest distance across the cross section) may be between 10 μm to 2 mm, or more preferably between 20 μm and 500 μm.

The first and second tube may be arranged in series. At least some of the first and further tubes may be arranged in series. The cross sectional area of at least one of the first, second and further tubes may vary along its length.

Features of any aspect of the invention may be combined with features of any other aspect of the invention.

Systems according to the invention can help to quickly characterize a variety of small samples of different fluid materials in research settings, such as in the discovery and manufacture of pharmaceuticals. They can also help to provide ongoing quality control and quality assurance in the manufacture of such materials.

DETAILED DESCRIPTION OF AN ILLUSTRATIVE EMBODIMENT

Figure 1:
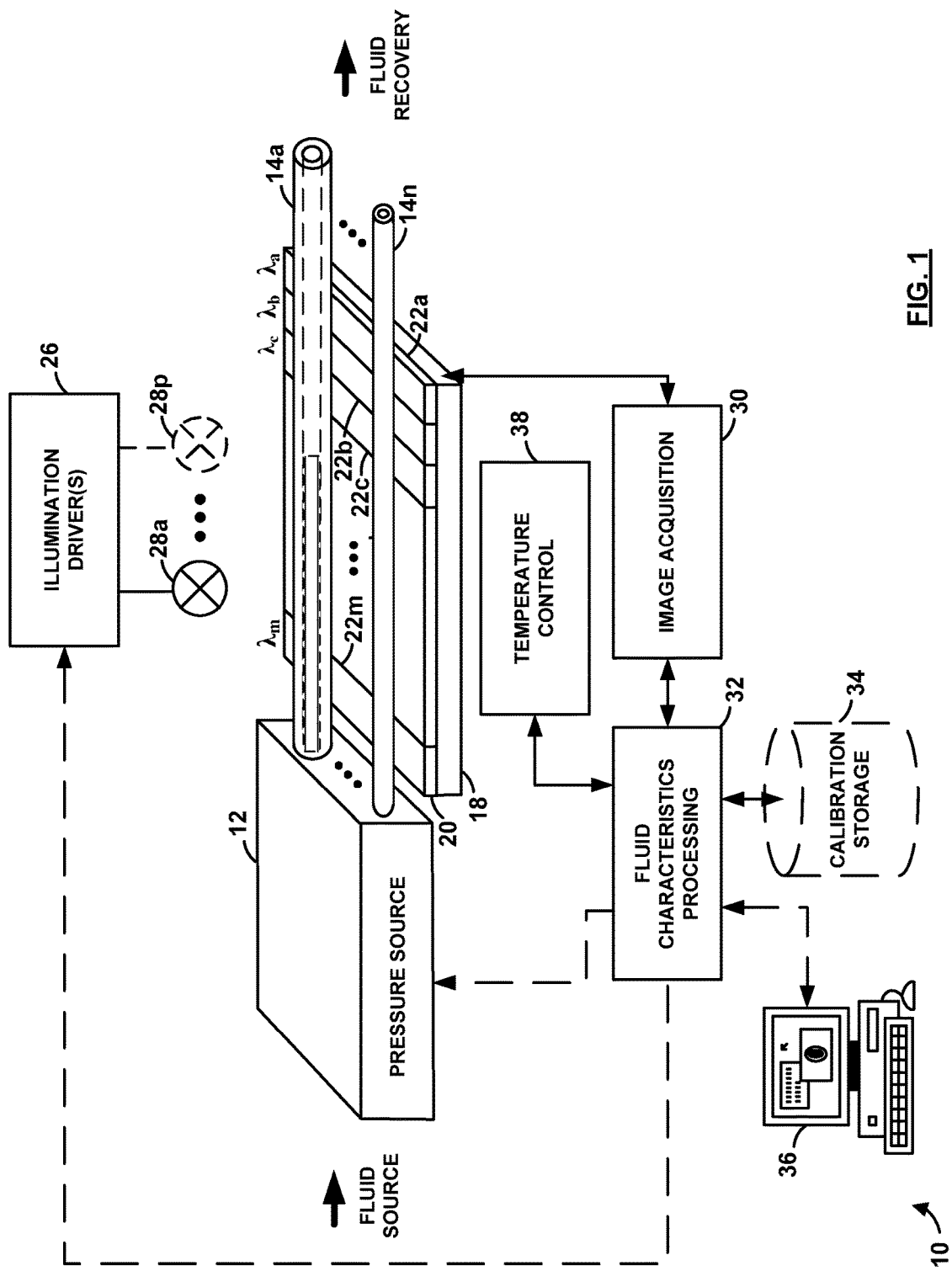
FIG. 1 is a block diagram of an embodiment of a fluid characterization system according to the invention, showing one capillary tube in phantom.

Referring to FIG. 1, an embodiment of a fluid characterization system 10 according to the invention characterizes fluids that are pressurized by a pressure source 12. The pressure source receives fluid at a fluid input and is hydraulically connected to one or more capillary tubes 14a . . . 14n. The capillary tubes in this embodiment preferably have different diameters and are preferably laid parallel on a two-dimensional array detector 18, although it is possible to position them in other ways. By keeping the capillary tubes proximate the detector, no lens is needed in this embodiment, although a lens or lens system and/or other optical elements could be provided between the capillary tubes and the two-dimensional detector array.

In this embodiment, the pressure source 12 produces negative pressure to draw the fluid along the capillary tubes from one end. The fluid can then be collected and recovered, if desired, at the other end of the tube. But the pressure source can also be a positive or reversible pressure source, as described below in connection with FIG. 2.

An optional optical filter 20, such as a low-pass filter, a high-pass filter, a band-pass filter, or a variable filter, can be positioned between the capillary tubes 14a . . . 14n and the two-dimensional array detector 18. In the case of a variable filter, the filter can be made up of a series of areas 22a . . . 22m each having a corresponding different wavelength characteristic λa . . . λm. These can span the detector in a direction perpendicular to the flow axis of the capillary tubes. In one embodiment, the variable filter is built by coating the detector itself. The use of a variable filter can allow the system to acquire a spectrum of the fluid, such as an absorption or emission spectrum, in addition to the other information it acquires. The use of variable filters and detector arrays is discussed in more detail in U.S. Pat. No. 6,690,464, which is herein incorporated by reference.

An image acquisition module 30 is operatively connected to an image data output of the two-dimensional detector array. The image acquisition module is operatively connected to a fluid characteristics processing module 32, which can be connected to calibration storage 34. In this embodiment, a general-purpose computer 36 is operatively connected to the fluid characteristics processing module and the image processing module. It should be noted that these parts of the system can be built using special-purpose hardware, and/or software running on a general-purpose processing platform. In the case of a larger bench-top instrument, for example, much of the image acquisition and fluid characteristics processing can be performed by a standard computer workstation, such as a Windows®-based PC. In the case of a smaller stand-alone or hand-held system, however, more of the image acquisition and fluid characteristics processing could be performed with dedicated hardware.

One or more dedicated illumination sources 28a . . . 28y and illumination drivers 26 can also be provided, although separate lamps or even ambient light could be used in some circumstances. The illumination sources can provide high intensity light to improve signal-to-noise performance of the system. In the preferred embodiments, the illumination drivers can provide a strobed drive signal to the illumination sources to set an effective frame rate and thereby provide precise strobed detection times. Examples of strobed illumination sources can include pulsed LEDs or chopped lasers.

In operation of the illustrative fluid characterization system 10, the pressure source 12 draws a fluid under test through the one or more capillary tubes 14a . . . 14n. The image acquisition module 30 causes the two-dimensional array detector 18 to acquire a series of images of the capillary tubes as the fluid advances through them. The images can be acquired in a number of different ways, depending on the architecture of the two-dimensional array detector 18, and whether strobing is employed. An array with a 500-1000 frame per second acquisition rate is currently believed to be well suited to this application although depending on the viscosity of the sample under test and the diameter of the capillary much lower frame rates will also work.

The fluid characteristic processing module 32 can first calculate the velocity at which the fluid passes through the capillary tubes 14a . . . 14n. This can be accomplished by multiplying the number of pixels advanced by the pixel pitch in the travel direction, and dividing the result by the time taken for that advance, which is equal to the number of frames multiplied by the frame rate. The reference used for this determination can be the meniscus of the fluid, although markers or other features could also be used. The velocity obtained for each tube can then be converted into viscosity based on one or more calibration factors obtained for one or more known fluid standards. Obtaining images that include samples and calibration standards is discussed in U.S. Pat. No. 7,391,025, which is herein incorporated by reference.

The system is preferably calibrated in one or more ways. One approach is to periodically run a known fluid standard with a known viscosity through the capillary tubes in the system, such as once a day or upon powering up the instrument. The resulting calibration factor compensates for offsets and drift, such as manufacturing variations in dimensions of the capillary tubes or drifts in temperature or power of the pressure source. Another approach is to provide one or more dedicated capillary tubes for the calibration fluid so that a series of images that contain both the sample and one or more calibration standards are obtained. This approach may be more accurate than a periodic calibration, because the calibration and measurement are made in exactly the same conditions. Other known types of calibration can also be performed on the system, such as a flat field calibration, which helps to compensate for variations between detectors in the array. Calibration may be unnecessary in some circumstances, however, such as where only a fairly low accuracy is needed, or where relative measurements are more important than absolute measurements.

If the system is equipped with a single capillary tube or more than one capillary tube of the same diameter, it can be used as a simple viscometer that can quickly measure the viscosity of a small sample. If the system is equipped with multiple capillary tubes of different diameters, the system can calculate viscosity values for each of these tubes. This allows the system to report a range of viscosity values, which can provide insight into non-Newtonian effects. In one embodiment, the viscosity values or derived shear values are presented in a plot against tube diameter, although they can be supplied as raw numbers or input as parameters in a more complex mathematical model. The tube diameter can be obtained from the manufacturer, it can be derived from its size in acquired images, or it can be determined in other ways.

The system should preferably also include temperature monitoring and/or control. Because viscosity is temperature dependent, measurements should preferably be performed at a predetermined temperature, or that the temperature be known, so that it can be compensated for. For this reason, a temperature control module 38 is provided in the system of FIG. 1. This control module ensures that the fluid under test and the measurement capillary tubes are all kept at the same predetermined temperature. In addition, the viscosity of the sample at different temperatures may be required to be determined and the same temperature control system can be used to accomplish this.

Different types and sizes of tubes can be used. In some embodiments the tube may be a capillary tube, but this is not essential, and other tubes may be used. The material of the tube is preferably transparent to a wavelength of light that the optical detectors are responsive to. The contact angle of a fluid sample with the internal surface of the tube may not limit the type of tube that is suitable. The tube may comprise a glass and/or polymeric material. The lumen through the tube may be circular, or may be another shape. For example, a rectangular and/or square cross section may be appropriate. The diameter (or longest distance across the cross section) may be between 10 μm to 2 mm, or more preferably between 20 μm and 500 μm.

In one embodiment, off-the-shelf capillary electrophoresis tubing is used, with inside diameters are on the order of 75 microns. The diameter of the capillary tubing is presently contemplated as being uniform along the length of the tubing, although it would also be possible to vary the diameter, such as by cascading different diameters of tubes to obtain serial measurements.

Figure 2:
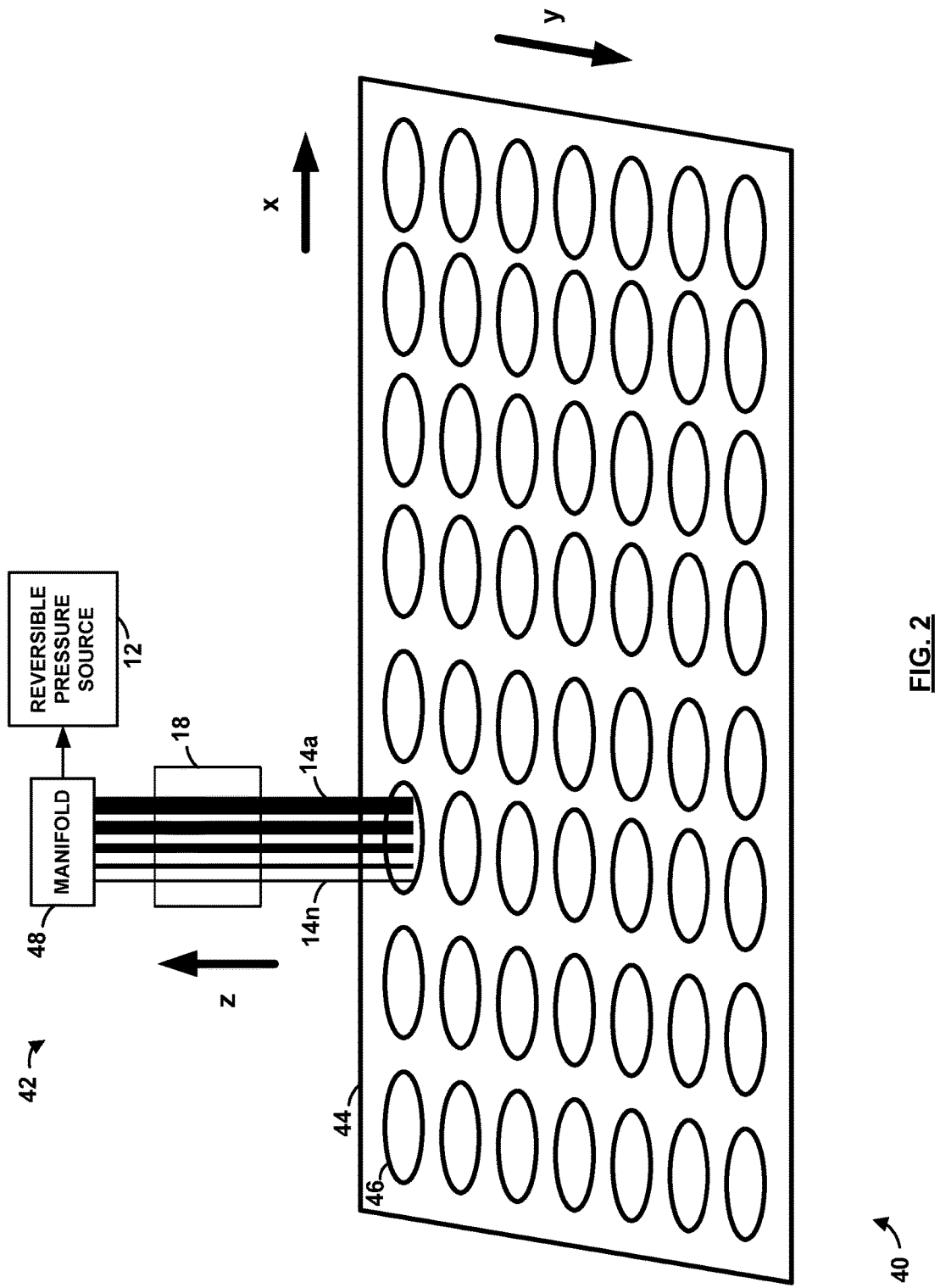
FIG. 2 is a block diagram of an embodiment of a high-throughput fluid characterization system according to the invention.

Referring to FIG. 2, an embodiment of a high-throughput fluid characterization system 40 according to the invention uses a probe 42 to perform successive measurements on a number of liquid samples held in different vessels, such as wells 46 of a multi-well plate 44 or carousel. The pressure source in this case is a reversible pressure source 12 that is hydraulically connected to one or more capillary tubes tubes 14a . . . 14n via a manifold 48. The capillary tubes are laid parallel on a two-dimensional array detector 18, although it is possible to position them in other ways. One or more of the tubes might snake back and forth in front of the detector, for example, if there is room. The ends of the capillary tubes can also be bundled together at their open ends to make the probe tip more compact and thereby fit into small sample vessels.

In this embodiment, an off-the-shelf x-y-z stage is provided to successively position the samples under the probe, although other types of mechanisms can be used to position the vessels and probe relative to each other. Wash and waste vessels can also be provided, either in the plate, or separately. Analysis and control logic, as described in connection with the system described in FIG. 1, can also be provided.

Figure 3:
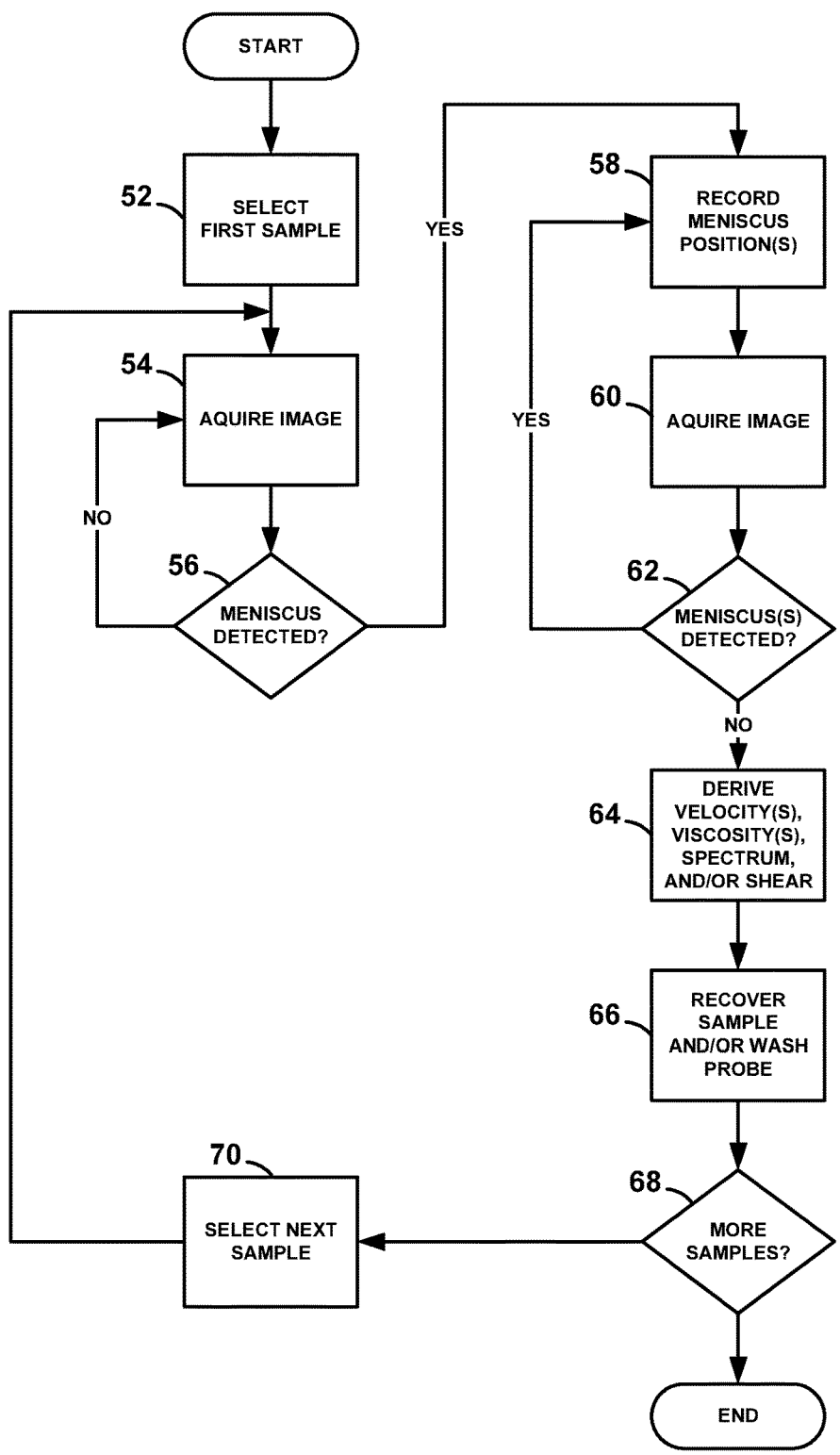
FIG. 3 is flowchart showing an illustrative method of operation for the embodiment of FIG. 2.

Referring also to FIG. 3, in an illustrative operation sequence 50, the x-y-z stage begins by positioning a first of the wells below the probe to select a first sample (step 52). The image acquisition module then acquires an image of the first sample (step 54). If no meniscus is detected in any of the capillary tubes (step 56), the system 40 continues to acquire images until a meniscus is detected in at least one of the capillary tubes.

When a meniscus is detected in one or more of the tubes, its position relative to the detectors in the array is recorded (step 58). Further images are then acquired (step 60) until no more meniscuses are detected in the images (step 62). The fluid characteristic processing module can then derive results for the first sample, such as one or more velocity, one or more viscosity, one or more spectrum, and/or one or more shear value (step 64).

The first sample can then be returned to the first well or it can be discarded into a waste well, and the probe can be washed in a wash well (step 66). If there are more samples to process (step 68), the x-y-z stage can select the next sample in the sequence (step 70). The process can then be repeated until there are no further samples to be tested, or some other condition is reached.

One of ordinary skill the art will recognize that there are a variety of ways to vary the illustrative operation sequence presented in connection with FIG. 3 without departing from the scope and spirit of the invention. The system might simply repeatedly acquire a series of images while the pump is on, and then look for images in which there is a meniscus in the resulting set of images. Or the system might acquire and store only a subset of the images, such as the first and last meniscus images for each capillary tube, and then process them all after the acquisition is complete for the whole set of samples.

The velocities can also be calculated a number of different ways. The velocity can be derived from time taken to span the whole detector, for example. Or instantaneous velocities in each successive frame pair could be calculated and then averaged. It is also possible to vary the pressure produced by the pump, such by steadily increasing the pressure in a ramp profile, and to then acquire a velocity profile instead of a single velocity for each capillary tube. The instantaneous meniscus velocity can also be monitored to ensure that the fluid is moving steadily, or it can even be used in a feedback loop to govern the speed of the pressure source.

Systems and methods according to the invention are particularly well suited to characterizing sample materials such as biomaterials, biopharmaceuticals or pharmaceutical formulations. A 96-well plate that holds a number of very small samples of biopharmaceutical candidate materials, for example, can be characterized to quickly narrow the field of materials under consideration. Or vessels can be loaded with one material diluted to different concentrations and/or held at different pH levels to more fully characterize that material. This can be particularly helpful where high viscosities in end products might prevent them from being injected and/or pumped.

Figure 4:
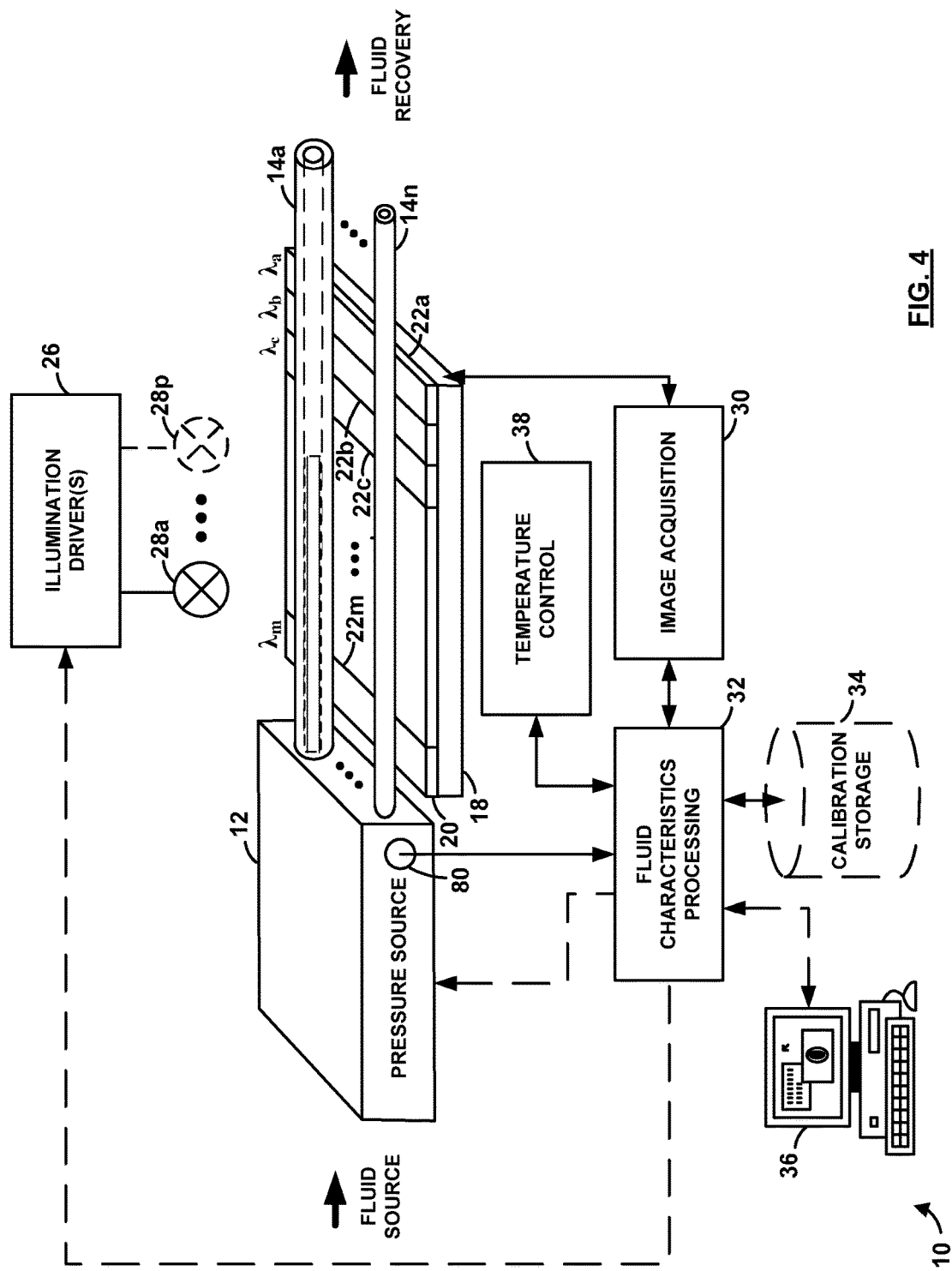
FIG. 4 is a block diagram of a second embodiment of a fluid characterization system according to the invention.

Referring to FIG. 4, a fluid characterization system according to the invention can also include a pressure sensor 80 that is responsive to the pressure produced by the pressure source 12, and can provide its output to the fluid characteristics processing module 32. This pressure sensor can be used in a feedback loop to keep the pressure in the system steady. The pressure sensor can also sample the pressure in synchrony with the acquisition of images and use the pressure measurements to correct the viscosity measurements for fluctuations in pressure.

Figure 5:
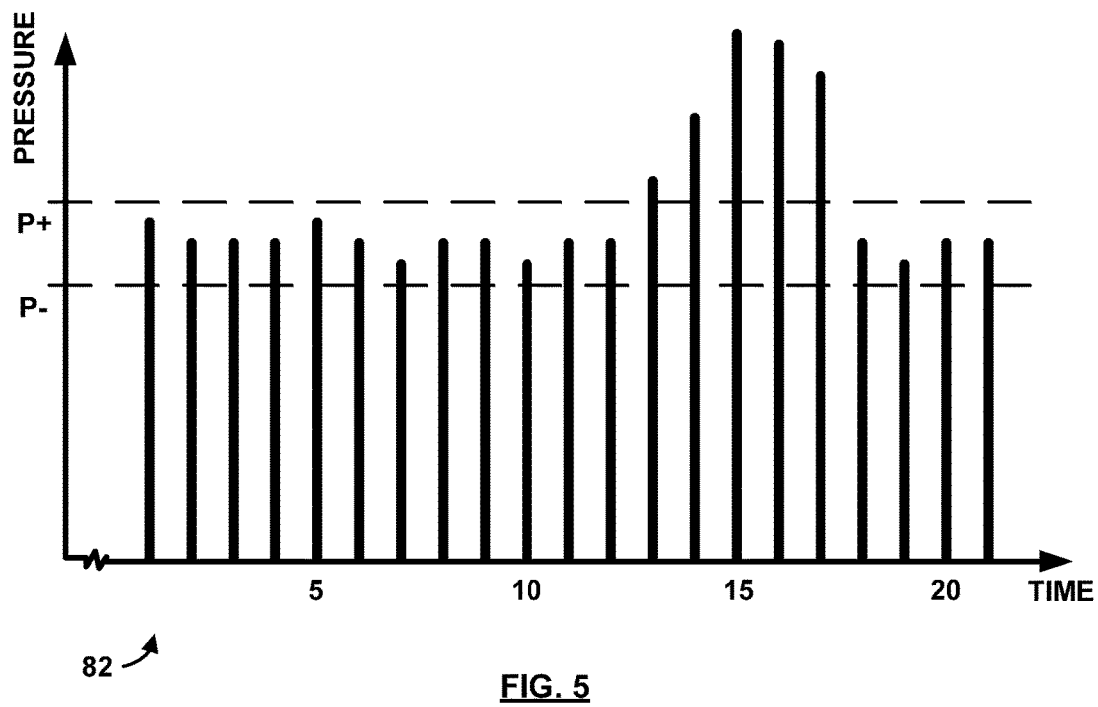
FIG. 5 is an illustrative plot of samples for explanation of the system of FIG. 4.

Referring to FIG. 5, another alternative is to use the pressure measurements to determine the quality of data being acquired and eliminate samples that are associated with outlying values. In an illustrative set of samples 82, for example, the system can determine whether samples fall below a preset minimum threshold P− or above a preset maximum threshold P+ and refrain from using data from the images acquired during those excursions (e.g., samples 13-17). Other monitoring methods are also possible. For example, the system can monitor the derivative of pressure and choose the most stable period or set of periods to perform viscosity measurements. The monitoring and discarding of samples can take place in real time or it can be performed on an acquired data set that includes a series of images and corresponding pressure values. Sampled temperature values can be included as well to provide a three-dimensional data set that can be corrected for pressure and temperature variations. In another embodiment, the acquisition of images can be gated by the pressure sensor, so that the system effectively waits for a stable period before performing a viscosity measurement.

Figure 6:
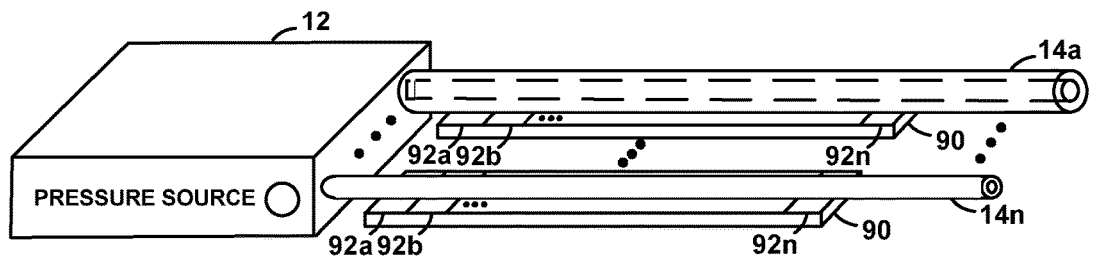
FIG. 6 is a block diagram of a portion of a third embodiment of a fluid characterization system according to the invention.

Referring to FIG. 6, a fluid characterization system according to the invention can also acquire successive images of the fluid under test using one dimensional arrays of detectors 92*a* . . . 92*n* provided from a series of separate one-dimensional detector array devices 90. This implementation of the system can be less expensive for a given resolution than if it were implemented using a two-dimensional detector array. In one embodiment, one-dimensional detector array devices designed for bar code readers are employed.

Figure 7:
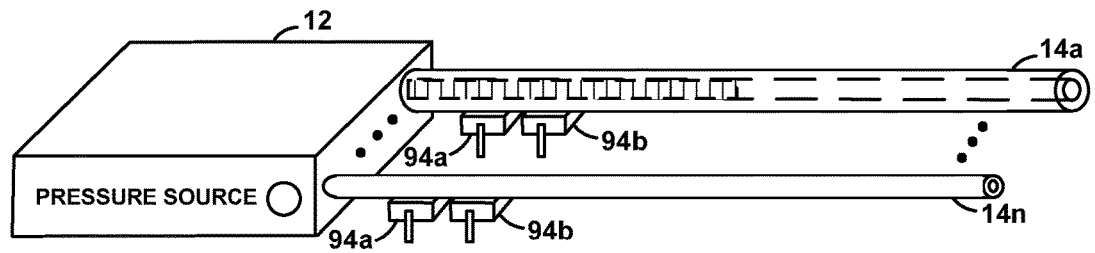
FIG. 7 is a block diagram of a portion of fourth embodiment of a fluid characterization system according to the invention.

Referring to FIG. 7, a fluid characterization system according to the invention can also acquire successive images of the fluid under test using detectors from pairs of point detector devices 94*a*, 94*b*, such as photodiodes, instead of two-dimensional or one-dimensional detector arrays. This implementation of the system can be even less expensive for a given resolution than if it were implemented using a one-dimensional detector array.

Individual point detectors can even be used in some types of systems. For example, a reference, such as water, and sample can be forced through adjacent capillary tubes that are each equipped with a single point detector. The relative velocity of the sample can then be derived from the transit times detected by the point detectors.

Figure 8:
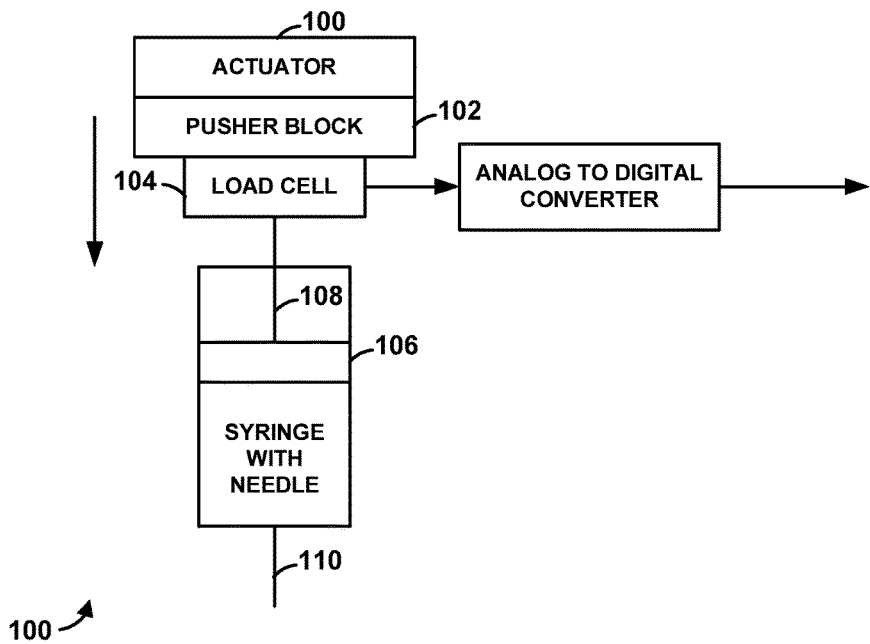
FIG. 8 is a block diagram of a portion of a fifth embodiment of a fluid characterization system according to the invention.

Referring to FIG. 8, a fluid characterization system according to the invention 100 can also employ an actuated syringe design. In this embodiment, an actuator 102, such as a stepper motor, is positioned to push a plunger 108 within a barrel 106 of a syringe that contains a sample of the fluid of interest while an applied force is measured. To accomplish this, a pusher block 102 and load cell 104 can be positioned between the actuator and a thumb rest of the plunger, although other actuating configurations could also be designed. In one embodiment, the load cell is a strain-gauge-based load cell for use in precision weighing scales with a resolution on the order of 0.01% of full-scale range.

In operation, the filled syringe is positioned in the apparatus and the actuator advances the pusher block. The load cell senses the applied force as the pusher block advances the plunger to drive the sample out through a needle of the syringe. A position sensor, such as an imaging array or a sensor that is built into the actuator, also records the position of the plunger as it advances. The load and position information can then be combined to derive a viscosity value for the sample.

This type of embodiment is particularly suitable for testing an injectable pharmaceutical preparation because its configuration operates under the preparation's intended conditions. The syringe and/or needle are therefore preferably similar or identical to the type of syringe and/or needle that is to be used with the preparation.

Fluid characterization systems according to the invention can employ stobed sources, as presented above. A single strobe mode allows for a shorter effective acquisition timing than the acquisition detectors may be able to support. This can result in clearer edge detection.

Figure 9:
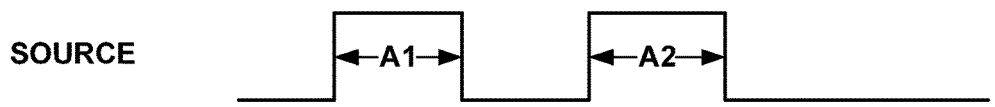
FIG. 9 is an illustrative waveform diagram for a multiply pulsed acquisition sequence for fluid characterization systems according to the invention.
Figure 9:
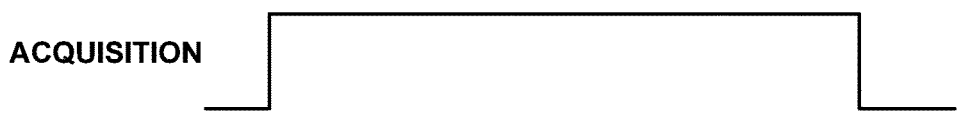
Figure 10:
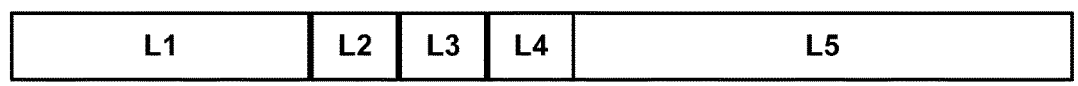
FIG. 10 is an illustrative diagram showing an image of a capillary tube corresponding to the multiply pulsed acquisition sequence of FIG. 9.
Figure 10:

Referring to FIGS. 9-10, a multiply strobed mode can also be used. If the source is pulsed twice during an acquisition cycle, for example, different parts of the tube will be exposed to light to different extents. During the first acquisition A1, the inlet side of the tube up to the first meniscus position at the beginning of the first acquisition (L1) will show as darkest. As the meniscus moves during the first acquisition period it will make a progressively lighter trace (L2). During the second acquisition period A2, the same process will be superimposed further away from the inlet side of the tube. The result is a set of successively darker traces (L1-L5) on the image that show where the meniscus was at two successive points in time.

Figure 11:
FIG. 11 is an illustrative waveform diagram for a multiply pulsed, multi-level acquisition sequence for fluid characterization systems according to the invention.
Figure 11:
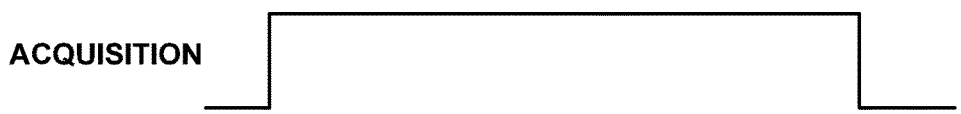
Figure 12:
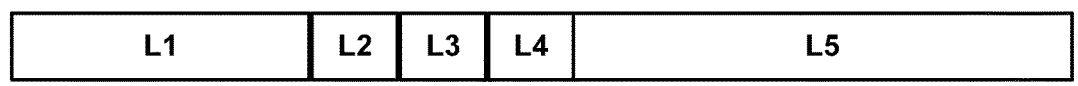
FIG. 12 is an illustrative diagram showing an image of a capillary tube corresponding to the multiply pulsed, multi-level acquisition sequence of FIG. 11.
Figure 12:

Referring to FIGS. 11-12, a multi-level mode can also be employed to improve the dynamic range of the instrument. This mode is similar to the multiply strobed mode described above, except that the pulses are of two or more different amplitudes H1, H2. This allows the system to select the measurements acquired with the pulses in which the illumination level is best suited to the opacity of the fluid. This can be particularly important where multiple capillary tubes are being imaged at once. In one embodiment, the intensity of the light passing through the sample can provide a measure of concentration of the sample.

The present invention has now been described in connection with a number of specific embodiments thereof. However, numerous modifications which are contemplated as falling within the scope of the present invention should now be apparent to those skilled in the art. For example, a multi-well probe could be devised to acquire samples from two or more wells at a time. Therefore, it is intended that the scope of the present invention be limited only by the scope of the claims appended hereto. In addition, the order of presentation of the claims should not be construed to limit the scope of any particular term in the claims.

The invention claimed is:

1. A capillary viscometer, comprising:
   a source of fluid pressure,
   a first capillary tube having an inside volume that is hydraulically responsive to the source of fluid pressure,
   one or more further capillary tubes each having an inside volume simultaneously responsive to the same source of fluid pressure that the first capillary tube is responsive to, wherein the inside volumes of the further capillary tubes are larger than the inside volume of the first capillary tube and different from each other,
   wherein the source of fluid pressure is configured to provide a common pressurized fluid to the inside volumes of the first and further tubes,
   a pressure transducer responsive to the source of fluid pressure,
   a two-dimensional array of optical detectors positioned proximate the first capillary tube with a first plurality of its detectors optically responsive to the inside volume of the first capillary tube and including an image data output,
   wherein the two-dimensional array of optical detectors is also positioned proximate the further capillary tubes with one or more further pluralities of its detectors optically responsive to the inside volume of the further capillary tubes,
   wherein the two-dimensional array detector includes at least 64 integrated detector elements along the first and further capillary tubes,
   wherein the two-dimensional detector is positioned to detect movement of the meniscus independent of any lenses,
   an acquisition driver circuit responsive to the image data output of the two-dimensional array to acquire a series of successive images of the inside volume of the first and further capillary tubes,
   viscosity computation logic responsive to the acquisition driver circuit and operative to compute the viscosity of the fluid from the succession of images of the inside volume of the first and further capillary based on a rate of detected movement of a meniscus in at least one of the capillary tubes, and
   viscosity value selection logic responsive to the pressure transducer and wherein the viscosity value selection logic is operative to select a viscosity value based on detected pressure levels.

2. The viscometer of claim 1 further including shear rate computation logic responsive to the acquisition driver circuit and operative to compute a shear rate of the fluid from the succession of images of the inside volumes of the first and second tubes.

3. The viscometer of claim 1 wherein the viscometer includes at least two of the further tubes.

4. The viscometer of claim 1 further including calibration storage for calibration information about a calibration run with a calibration standard, and where the viscosity computation logic is responsive to the calibration information stored in the calibration storage.

5. The viscometer of claim 1 further including at least one calibration tube having an inside volume that is hydraulically responsive to at least one source of a known fluid standard and wherein the two-dimensional array of optical detectors includes a plurality of detectors that are optically responsive to the inside volume of the calibration tube.

6. The viscometer of claim 1 wherein the first tube has a diameter below 500 um.

7. The viscometer of claim 1 further including a filter positioned in an optical path between the first tube and the first array of optical detectors.

8. The viscometer of claim 1 further comprising a pressure transducer responsive to the source of fluid pressure.

9. The viscometer of claim 8 wherein the viscosity computation logic is responsive to the pressure transducer and is operative to compute a pressure-corrected viscosity.

10. The viscometer of claim 1 wherein the viscosity value selection logic is operative to exclude outliers.

11. The viscometer of claim 1 wherein the viscosity value selection logic is operative to seek stable periods.

12. The viscometer of claim 1 further including a strobed illumination source to illuminate at least one of the tubes.

13. The viscometer of claim 1 further including a multi-level strobed illumination source to illuminate at least one of the tubes.

14. The viscometer of claim 1 further including reporting logic operative to report results of the viscosity computations for the first and further capillaries to provide insight into non-Newtonian effects.

15. The viscometer of claim 14 wherein the reporting logic is operative to report results of derived shear values for the first and further capillaries in a plot against tube diameter.

16. A capillary viscometry method, comprising:
driving a fluid under test through an inside volume of a first capillary tube,
driving the same fluid under test through an inside volume of one or more further capillary tubes, wherein the inside volumes of the further capillary tubes are larger than the inside volume of the first capillary tube and different from each other,
acquiring successive images of the same fluid under test in the first and further tubes as it advances through the inside volume of the first capillary tube and further capillary tubes, and
deriving a range of different viscosity values of the same fluid under test from the successive acquired images of the fluid under test as it advances through the inside volume of the first capillary tube and further capillary tubes, and
reporting results of the step of deriving in a manner that provides insight into non-Newtonian effects in the fluid under test.

17. The method of claim 16 further comprising acquiring a succession of pressure values for the fluid under test, wherein deriving the viscosity of the fluid under test is performed based on the successive images of the fluid under test and the succession of pressure values.

18. The method of claim 16, further including the step of recovering the fluid under test from the first tube after the step of acquiring.

19. The method of claim 16 wherein the method is operative to derive a viscosity of a sample of less than 10 microliters.

20. The method of claim 16 wherein the step of driving is performed at different pressures.

21. The method of claim 16 wherein the step of reporting reports results of the viscosity computations for the first and further capillaries in a plot against tube diameter.

22. The method of claim 16 wherein the step of acquiring detects at least 64 pixels along the length of first and further capillary tubes.

23. The method of claim 16 wherein the step of acquiring acquires two-dimensional images.

24. The method of claim 16 wherein the step of acquiring successive images of the same fluid under test includes acquiring a series of images of the fluid under test as it passes through a series of varied capillary diameters.

25. The method of claim 24 wherein the step of acquiring successive images of the same fluid under test includes acquiring images of the fluid under test as it passes through a series of cascaded capillary tubes of different diameters.

26. The method of claim 16 wherein the step of acquiring successive images of the same fluid under test acquires successive images of a the fluid as it passes through a plurality of parallel capillary tubes of different diameters.

27. A capillary viscometer, comprising:
means for driving a fluid under test through an inside volume of a first capillary tube, and driving the same fluid under test through an inside volume of one or more further capillary tubes, wherein the inside volumes of the further capillary tubes are larger than the inside volume of the first capillary tube and different from each other,
means for acquiring successive images of the same fluid under test in the first and further tubes as it advances through the inside volume of the first capillary tube and further capillary tubes,
means for deriving a range of different viscosity values of the same fluid under test from the successive acquired images of the fluid under test as it advances through the inside volume of the first capillary tube and further capillary tubes, and
reporting means responsive to the means for deriving for providing insight into non-Newtonian effects in the fluid under test.

28. The viscometer of claim 27 wherein the reporting means are operative to report results of derived shear values for the first and further capillaries in a plot against tube diameter.

29. The viscometer of claim 27 wherein the means for acquiring includes a two-dimensional array detector and wherein the first and further tubes are arranged in parallel on the two-dimensional array detector.

30. The viscometer of claim 27 wherein the first and further tubes are cascaded to obtain serial measurements.

31. The viscometer of claim 27 further including shear rate computation logic responsive to the means for acquiring and operative to compute a shear rate of the fluid from the succession of images of the inside volumes of the first and second tubes.

32. The viscometer of claim 27 wherein the viscometer includes at least two of the further tubes.

33. The viscometer of claim 27 further including calibration storage for calibration information about a calibration run with a calibration standard, and where the means for deriving is responsive to the calibration information stored in the calibration storage.

34. The viscometer of claim 27 further including at least one calibration tube having an inside volume that is hydraulically responsive to at least one source of a known fluid standard and wherein the means for acquiring includes a plurality of detectors that are optically responsive to the inside volume of the calibration tube.

35. The viscometer of claim 27 wherein the first tube has a diameter below 500 um.

36. The viscometer of claim 27 further including a filter positioned in an optical path between the first tube and the means for acquiring.

37. The viscometer of claim 27 further comprising a pressure transducer responsive to the means for driving.

38. The viscometer of claim 37 wherein the means for deriving is responsive to the pressure transducer and is operative to compute a pressure-corrected viscosity.

39. The viscometer of claim 27 further including a strobed illumination source to illuminate at least one of the tubes.

40. The viscometer of claim 27 further including a multilevel strobed illumination source to illuminate at least one of the tubes.

41. The viscometer of claim 27 wherein the means for acquiring includes a two-dimensional array of optical detectors.

42. The viscometer of claim 27 wherein the means for acquiring includes at least 64 integrated detector elements along the first and further capillary tubes.

* * * * *